United States Patent
McAuley et al.

(10) Patent No.: US 11,821,345 B2
(45) Date of Patent: Nov. 21, 2023

(54) SYSTEMS AND METHODS FOR LUBRICANT DILUTION DETECTION

(71) Applicant: Caterpillar Inc., Peoria, IL (US)

(72) Inventors: Ben McAuley, Mount Warren Park (AU); Tyler P. Jewell, Oreana, IL (US); Michael J. Campagna, Chillicothe, IL (US); Andrew W. Billing, Bloomington, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 17/652,802

(22) Filed: Feb. 28, 2022

(65) Prior Publication Data

US 2022/0307395 A1    Sep. 29, 2022

Related U.S. Application Data (60) Provisional application No. 63/165,593, filed on Mar. 24, 2021.

(51) Int. Cl.
     *F01M 1/18*      (2006.01)
     *F01M 11/10*      (2006.01)
     (Continued)

(52) U.S. Cl.
     CPC ............... *F01M 1/18* (2013.01); *F01M 1/20* (2013.01); *F01M 11/10* (2013.01);
     (Continued)

(58) Field of Classification Search
None
See application file for complete search history.

(56) References Cited

U.S. PATENT DOCUMENTS 5,433,105 A   *   7/1995   Takahashi ............... G01N 25/14
                                                                      73/61.46
5,950,591 A   *   9/1999   Kageyama ....... C10M 175/0091
                                                                        184/2

(Continued)

FOREIGN PATENT DOCUMENTS

CN          102337975 A   *   2/2012   ............. F01N 9/002
CN          105507983 A   *   4/2016   ............... F01M 5/02
(Continued)

OTHER PUBLICATIONS

Written Opinion and International Search Report for Int'l. Patent Appln. No. PCT/US2022/021460, dated Jun. 29, 2022 (7 pgs).

*Primary Examiner* — Kevin R Steckbauer (57) ABSTRACT

Systems and methods for lubricant dilution detection are disclosed. A method for detecting lubricant dilution for a lubrication system includes detecting a low idle condition. The method includes receiving sensed values indicative of lubricant pressure and lubricant temperature during the low idle condition. The method also includes determining a lubricant pressure threshold based on the sensed value indicative of lubricant temperature. The method further includes determining lubricant dilution based on the sensed value indicative of lubricant pressure and the determined lubricant pressure threshold during the low idle condition. In accordance with a determination that there is lubricant dilution, the method includes outputting an indication of the lubricant dilution.

20 Claims, 4 Drawing Sheets

(51) Int. Cl.
*G01N 33/28* (2006.01)
*F01M 1/20* (2006.01)

(52) U.S. Cl.
CPC ... *G01N 33/2888* (2013.01); *F01M 2011/142* (2013.01); *F01M 2011/146* (2013.01); *F01M 2011/148* (2013.01); *F01M 2011/1446* (2013.01); *F01M 2011/1473* (2013.01); *F01M 2250/60* (2013.01); *F02D 2200/023* (2013.01); *F02D 2200/024* (2013.01); *F02D 2250/11* (2013.01); *F16N 2200/00* (2013.01); *F16N 2200/10* (2013.01); *F16N 2200/20* (2013.01); *F16N 2250/04* (2013.01); *F16N 2250/08* (2013.01); *F16N 2250/16* (2013.01); *G01N 33/2841* (2013.01); *G01N 33/2847* (2013.01); *G01N 33/2852* (2013.01)

(56) References Cited

U.S. PATENT DOCUMENTS

| | | | |
|---|---|---|---|
| 8,109,138 B2* | 2/2012 | Han | G01N 11/06 |
| | | | 73/114.55 |
| 8,734,122 B2 | 5/2014 | Murray et al. | |
| 9,394,843 B2* | 7/2016 | Hakeem | F02D 41/0007 |
| 10,202,911 B2* | 2/2019 | Cunningham | F02D 13/08 |
| 10,233,799 B2* | 3/2019 | Ogata | H05B 1/0236 |
| 2003/0196479 A1* | 10/2003 | Kasen | G01N 33/2888 |
| | | | 73/53.01 |
| 2016/0102623 A1* | 4/2016 | Hakeem | F01M 5/04 |
| | | | 701/113 |
| 2019/0195095 A1 | 6/2019 | Dudar | |
| 2022/0307395 A1* | 9/2022 | McAuley | F01M 1/18 |

FOREIGN PATENT DOCUMENTS

| | | | | |
|---|---|---|---|---|
| CN | 108506114 A | | 9/2018 | |
| CN | 105507983 B | * | 11/2019 | .............. F01M 5/02 |
| DE | 10201878 A1 | * | 7/2003 | ........ B60R 16/0232 |
| DE | 10201878 B4 | * | 4/2010 | ........ B60R 16/0232 |
| DE | 102015117117 A1 | * | 4/2016 | .............. F01M 5/02 |
| EP | 1908947 A2 | * | 4/2008 | .......... F02D 41/024 |
| EP | 2639420 A1 | * | 9/2013 | .......... F02D 41/028 |
| EP | 1908947 B1 | * | 12/2017 | .......... F02D 41/024 |
| EP | 2639420 B1 | * | 2/2021 | .......... F02D 41/028 |
| JP | 2004-293394 A | | 10/2004 | |
| JP | 2004340090 A | * | 12/2004 | |
| JP | 2006046245 A | * | 2/2006 | |
| JP | 2008111428 A | * | 5/2008 | .......... F02D 41/024 |
| JP | 2010180774 A | * | 8/2010 | |
| JP | 4905303 B2 | * | 3/2012 | .......... F02D 41/024 |
| JP | 2014098360 A | * | 5/2014 | |
| JP | 2014098360 A | | 5/2014 | |
| JP | 2014129733 A | | 7/2014 | |
| JP | 2015168379 A | | 9/2015 | |
| JP | 2016130506 A | | 7/2016 | |
| JP | 6176159 B2 | | 7/2017 | |
| JP | 2019147539 A | | 9/2019 | |
| JP | 2020-133535 A | | 8/2020 | |
| RU | 2701246 C2 | * | 9/2019 | .............. F01M 5/02 |
| WO | 2008/071639 A1 | | 6/2008 | |
| WO | WO-2022148750 A1 | * | 7/2022 | |
| WO | WO-2022204226 A1 | * | 9/2022 | .............. F01M 1/18 |

* cited by examiner

SYSTEMS AND METHODS FOR LUBRICANT DILUTION DETECTION

CROSS-REFERENCE TO RELATED APPLICATION(S)

This application claims the benefit of priority under 35 U.S.C. § 119 to U.S. Provisional Patent Application No. 63/165,593, filed on Mar. 24, 2021, the entirety of which is incorporated herein by reference.

TECHNICAL FIELD

The present disclosure relates generally to lubrication systems, and more particularly, to systems and methods for lubricant dilution detection for such lubrication systems.

BACKGROUND

Lubrication systems may provide one or more pressurized lubricants to various moving components (e.g., bearings, gears, etc.) to lubricate the components. Lubricants, such as oil, used in the lubrication systems may become diluted over time due to various causes. For example, liquid fuel (e.g., diesel fuel) from a fuel system of an engine and/or coolant from an oil cooler may leak into the lubrication system and become mixed with the lubricant. Consequently, the viscosity, and thus the lubrication ability, of the lubricant may be reduced. Accordingly, the moving components may become damaged over time due the diluted lubricant. Current methods for detecting lubricant dilution may not adequately detect dilution of the lubricant and/or may falsely diagnose dilution of the lubricant.

PCT Application Publication No. WO2008/071639, published on Jun. 19, 2008 ("the '639 publication"), describes a method for determining oil quality in an oil supply line. At least one temperature and at least one pressure in the oil supply line are measured, and information is generated to determine a volumetric flow through the oil supply line. Information about the oil quality, such as oil dilution, is generated from the measured temperature, the measured pressure, and the volumetric flow. However, the method of the '639 publication may not adequately detect lubricant dilution and/or may falsely diagnose dilution of the lubricant.

The systems and methods for lubricant dilution detection of the present disclosure may solve one or more of the problems set forth above and/or other problems in the art. The scope of the current disclosure, however, is defined by the attached claims, and not by the ability to solve any specific problem.

SUMMARY

In one aspect, a method for detecting lubricant dilution for a lubrication system is disclosed. The method includes: detecting a low idle condition; receiving sensed values indicative of lubricant pressure and lubricant temperature during the low idle condition; determining a lubricant pressure threshold based on the sensed value indicative of lubricant temperature; determining lubricant dilution based on the sensed value indicative of lubricant pressure and the determined lubricant pressure threshold during the low idle condition; and in accordance with a determination that there is lubricant dilution, outputting an indication of the lubricant dilution.

In another aspect, a lubricant dilution detection system is disclosed. The system includes: a lubrication system; a lubricant pressure sensor for sensing values indicative of lubricant pressure in the lubrication system; a lubricant temperature sensor for sensing values indicative of lubricant temperature in the lubrication system; and a controller configured to: detect a low idle condition; receive the sensed values indicative of lubricant pressure and lubricant temperature during the low idle condition; determine a lubricant pressure threshold based on the sensed value indicative of lubricant temperature; determine lubricant dilution based on the sensed value indicative of lubricant pressure and the determined lubricant pressure threshold during the low idle condition; and in accordance with a determination that there is lubricant dilution, output an indication of the lubricant dilution.

In yet another aspect, a method for detecting lubricant dilution for a lubrication system is disclosed. The method includes: detecting a low idle condition of the engine when an engine speed is substantially equal to a low idle engine speed threshold; receiving sensed values indicative of lubricant pressure and lubricant temperature during the low idle condition; determining a lubricant pressure threshold based on the sensed value indicative of lubricant temperature, wherein the lubricant pressure threshold is a variable threshold including different threshold values for different values indicative of lubricant temperature; determining whether the sensed value indicative of lubricant pressure is less than the determined lubricant pressure threshold during the low idle condition; in accordance with a determination that the sensed value indicative of lubricant pressure is less than the determined lubricant pressure threshold, determining lubricant dilution; and in accordance with a determination that there is lubricant dilution, outputting an indication of the lubricant dilution.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Both the foregoing general description and the following detailed description are exemplary and explanatory only and are not restrictive of the features, as claimed. As used herein, the terms "comprises," "comprising," "has," "having," "includes," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, unless stated otherwise, relative terms, such as, for example, "about," "substantially," and "approximately" are used to indicate a possible variation of ±10% in the stated value.

Figure 1:
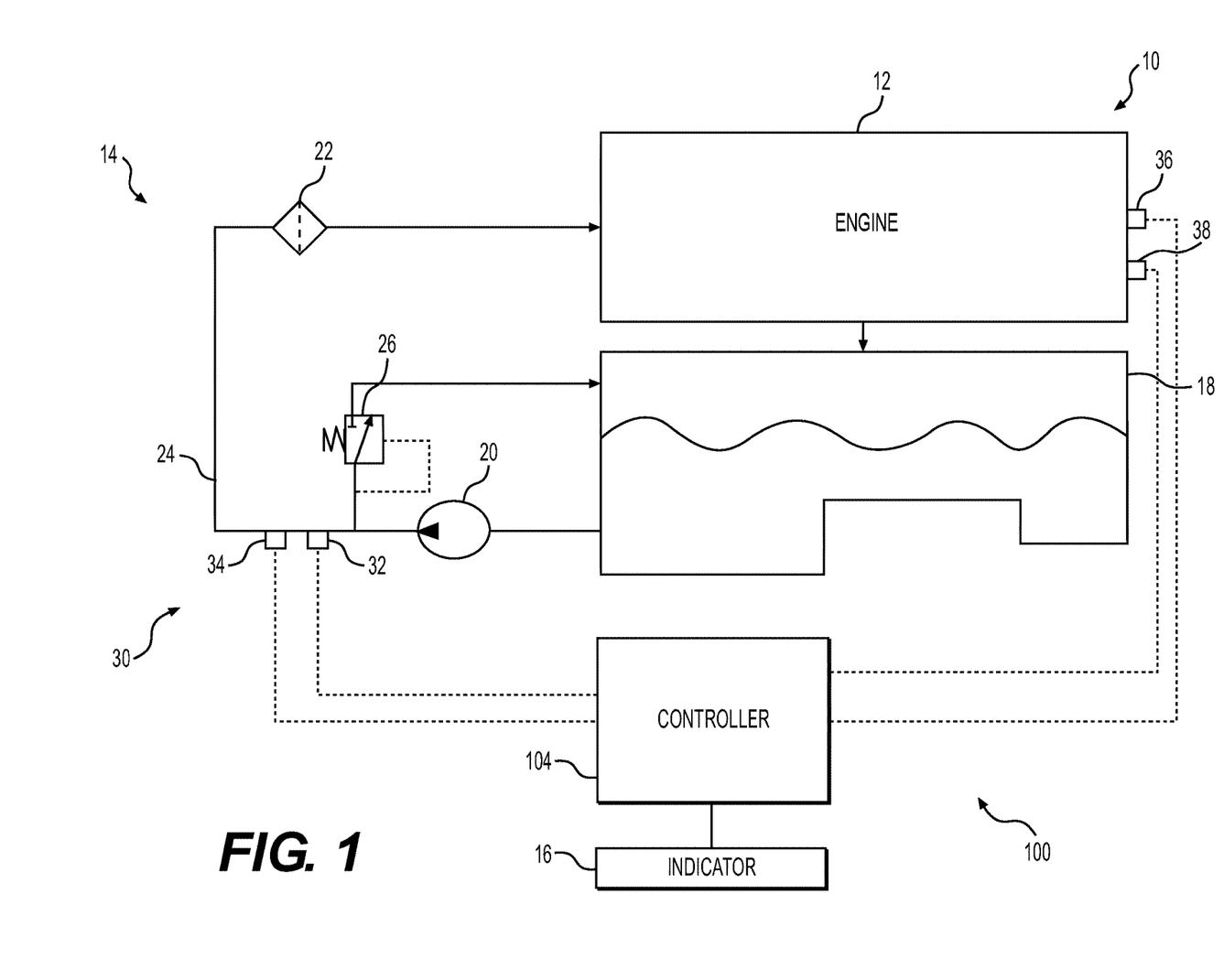
FIG. 1 is a schematic view of an engine system having a lubricant dilution detection system, according to aspects of the disclosure.

FIG. 1 illustrates a schematic view of an engine system 10 system having a lubricant dilution detection system 100. Engine system 10 includes an engine 12, such as an internal combustion engine. Engine 12 may include for example, a diesel engine, a gasoline engine, a dual fuel engine (e.g., an engine capable of running on both gaseous fuel and/or liquid fuel), or any other type of engine known in the art. Engine 12 may be used in power generator applications, mobile machines (e.g., vehicles), other types of heavy machinery or equipment, or the like. Operation of engine 12 may produce power. For example, engine 12 may include one or more cylinders (not shown) and a crankshaft (not shown) for providing power to a flywheel (not shown) or the like. As shown in FIG. 1, engine system 10 also includes a lubrication system 14, a lubricant dilution detection system 100, and an output indicator 16. Engine system 10 may include other components and/or systems, such as, for example, a transmission system and/or other mechanical systems including moving and/or rotating components.

Lubrication system 14 may include a lubricant supply 18, such as a lubricant pan, a pump 20, and a filter 22 in communication with each other via a lubricant supply line 24 (e.g., lubricant gallery). The lubricant may include oil or any other type of liquid lubricant known in the art. Pump 20 may include a mechanical pump for pressurizing fluid (e.g., lubricant) to generate flow of lubricant from lubricant supply 18 through lubrication system 14. For example, pump 20 may include a gear-type pump driven by gear trains from the crankshaft or other rotating component of engine 12. Further, pump 20 may be driven by other means and may include, for example, an electric driven pump, a hydraulic driven pump, and/or any other type of pump. Pump 20 may include a pressure regulator valve 26 for reducing and regulating a pressure of the lubricant exiting pump 20 and lowering the pressure to a predetermined level, as detailed further below. Valve 26 may receive pressure signals from lubricant supply line 24 (e.g., as shown by the dashed lines connected to valve 26), such that valve 26 is controllable by the pressure signals between an open position and a closed position for regulating the pressure at the predetermined level.

Lubricant supply line 24 may include a series of pipes or passageways for supplying lubricant from lubricant supply 18 to various components of engine 12. For example, lubrication system 14 may supply lubricant to the crankshaft, the pistons, a camshaft (not shown), bearings (not shown), and/or any other components of engine 12. Excess lubricant may drain back into lubricant supply 18. Filter 22 may remove particulates or other contaminants from the lubricant to prevent the particulates or contaminants from damaging components of engine 12. It is understood that lubrication system 14 may include any number and/or combination of valves or other components known in the art, such as one or more lubricant coolers (not shown), a scavenge pump (not shown), a pressure relief valve, and/or other types of filters (e.g., suction screen and/or centrifugal lubricant filter). Further, while the exemplary embodiment describes a lubrication system 14 for an engine 12, it is understood that aspects of the disclosure may be used for lubrication systems for any other type of mechanical system having moving and/or rotating components (e.g., transmission systems).

Output indicator 16 may indicate lubrication dilution in lubrication system 14, as detailed below. Output indicator 16 may include a display, a gauge, a light, a speaker, or the like. For example, output indicator 16 may indicate a value (numerical value, percentage, or the like) indicative of dilution of the lubricant in lubrication system 14 and/or may indicate (e.g., via a notification) when the lubricant is diluted. Indicator 16 may be located as part of engine system 10 (e.g., in an operator cab of a mobile machine) and/or may be located remote from engine system 10. While only a single output indicator 16 is described herein, it is understood that output indicator 16 may include one or more indicators and may include any type of indicator for indicating lubricant dilution in lubrication system 14.

Lubricant dilution detection system 100 includes a controller 104, such as an engine control module (ECM), and a sensor system 30 connected to controller 104. Sensor system 30 may include one or more sensors for measuring operating conditions, such as pressure sensors, temperature sensors, flow sensors, speed sensors, or the like. For example, sensor system 30 may include a lubricant pressure sensor 32, a lubricant temperature sensor 34, an engine speed sensor 36, and/or an exhaust temperature sensor 38. Lubricant pressure sensor 32 may be located in lubricant supply line 24 downstream of pump 20 and may sense values indicative of a pressure of lubricant in lubrication system 14. Lubricant temperature sensor 34 may be located in lubricant supply line 24 downstream of pump 20 and may sense values indicative of temperature of lubricant in lubrication system 14. For example, lubricant temperature sensor 34 may sense a temperature of the lubricant directly. In some embodiments, lubricant temperature sensor 34 may sense a temperature of coolant in a cooling system (not shown) of engine system 10. The temperature of the coolant may correspond to a temperature of the lubricant. Engine speed sensor 36 may be located at the crankshaft of engine 12 and may sense values indicative of engine speed. Engine speed sensor 34 may be located at any location of engine 12, such as, for example, a crank pulley, the flywheel, a camshaft, or on the crankshaft. Exhaust temperature sensor 38 may be located in an exhaust system (not shown) of engine system 10 and may sense values indicative of a temperature of exhaust in the exhaust system. It is understood that sensors 32, 34, 36, 38 may include any type of sensor such as resistive sensors, inductive sensors, capacitive sensors, piezoelectric sensors, optical sensors, micro electro-mechanical system sensors, or the like. Further, sensor system 30 may include physical sensors and/or virtual sensors (e.g., sensors that determine a value indirectly by controller 104 based on other sensed values) and may include any number and/or combination of sensors as necessary for sensing or measuring operating conditions.

Figure 2:
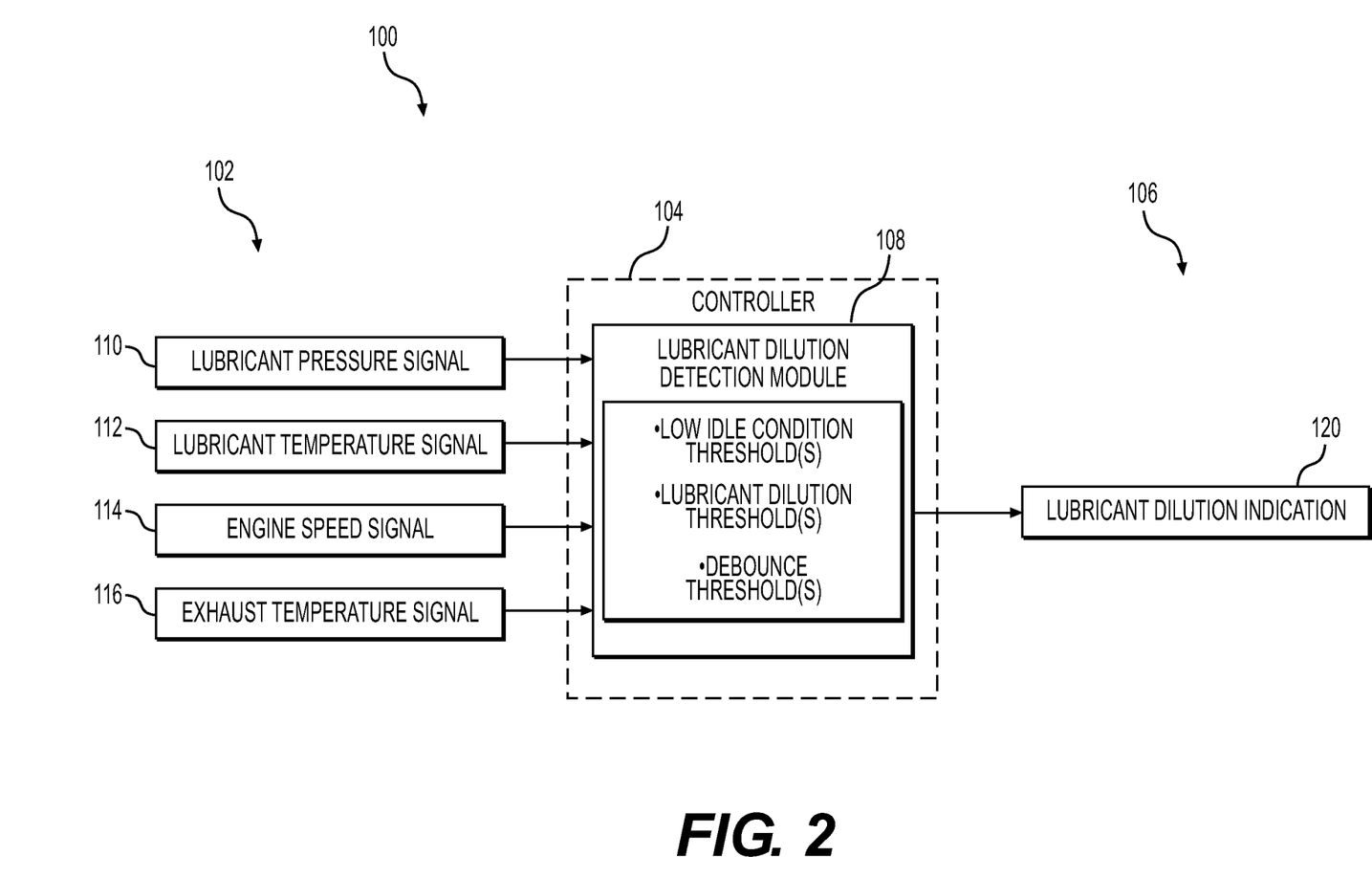
FIG. 2 is a schematic view of the exemplary lubricant dilution detection system for the engine system of FIG. 1.

FIG. 2 illustrates a schematic view of the exemplary lubricant dilution detection system 100 for operation and/or control of at least portions of engine system 10. System 100 may include inputs 102, controller 104, and outputs 106. Inputs 102 may include, for example, lubricant pressure signal 110 from pressure sensor 32, lubricant temperature signal 112 from temperature sensor 34, engine speed signal 114 from speed sensor 36, and exhaust temperature signal 116 from temperature sensor 38. Outputs 106 may include, for example, a lubricant dilution indication signal 120. Controller 104 also includes a lubricant dilution detection module 108. Lubricant dilution detection module 108 may receive inputs 102, implement a method 300 for detecting dilution of lubricant in lubrication system 14 and control outputs 106, as described with reference to FIG. 3 below.

Controller 104 may embody a single microprocessor or multiple microprocessors that may include means for detecting dilution of lubricant in lubrication system 14. For example, controller 104 may include a memory, a secondary storage device, and a processor, such as a central processing unit or any other means for accomplishing a task consistent with the present disclosure. The memory or secondary storage device associated with controller 104 may store data and/or software routines that may assist controller 104 in performing its functions, such as the functions of method 300 of FIG. 3. Further, the memory or secondary storage device associated with controller 104 may also store data received from the various inputs 102 associated with lubricant dilution detection system 100. Numerous commercially available microprocessors can be configured to perform the functions of controller 104. It should be appreciated that controller 104 could readily embody a general machine controller capable of controlling numerous other machine functions. Further, controller 104, or portions thereof, may be located remote from engine system 10. Various other known circuits may be associated with controller 104, including signal-conditioning circuitry, communication circuitry, hydraulic or other actuation circuitry, and other appropriate circuitry.

Controller 104 may also include stored values for use by module 108. For example, the stored values may include low idle condition thresholds, lubricant dilution thresholds, and debounce thresholds. Low idle condition thresholds may include one or more thresholds for various operating conditions of engine system 10 that indicate a low idle condition for engine system 10. As used herein, "low idle condition" is a minimum operating condition of the engine 12 in which the engine is uncoupled from a load of engine system 10 or out of gear (e.g., engine 12 is disconnected from a drivetrain of engine system 10). For example, when the engine 12 is operating at the low idle condition, the engine speed may be set at a minimum constant engine speed (e.g., an idle speed) such that the engine system 10 is running, but the engine 12 is disconnected from a load. During the low idle condition, engine speed may decrease such that pump 20 decreases lubricant pressure. Accordingly, valve 26 is closed during the low idle condition and the lubricant pressure is not regulated, as further detailed below. Engine system 10 may also include a high idle condition during which the engine speed is greater than the engine speed during the low idle condition. For example, the engine speed during the high idle condition may be between 1800-1960 RPM. During the high idle condition, valve 26 may be open to regulate lubricant pressure, as detailed further below. The low idle condition thresholds may include, for examine, predetermined values of various operating conditions. For example, the low idle condition thresholds may include a threshold for engine speed (e.g., 700 RPM), a threshold for engine load (e.g., about zero), fuel pressure (e.g., 50 kPa), or any other threshold/predetermined value of other operating conditions for indicating low idle. It is understood that the threshold values are exemplary, and the thresholds for engine speed, engine load, and/or fuel pressure may include any threshold value as necessary for a respective application.

The lubricant dilution thresholds may include one or more thresholds for indicating lubricant dilution for lubrication system 14. For example, the lubricant dilution thresholds may include one or more lubricant pressure thresholds. The one or more lubricant pressure thresholds may include a variable threshold as a function of lubricant temperature. For example, the one or more lubricant pressure thresholds may include different lubricant pressure thresholds for different lubricant temperatures provided in a map or lookup table. The information used to derive the values of the map or lookup table may be determined by empirical analysis. Such empirical data may be obtained, for example, by operating a test engine system 10 under predetermined conditions (e.g., under particular operating conditions) during, for example, bench testing. For example, the threshold values may be correlated to the values of the lubricant temperature. Thus, the lubricant pressure threshold is determined based on a map representative of empirical data of lubricant pressure threshold values with respect to lubricant temperature. While the exemplary embodiment details the lubricant pressure threshold values as a function of lubricant temperature, it is understood that the map or lookup table may provide a variable threshold as a function of coolant temperature and other various inputs (e.g., other operating conditions) and/or values indicative of lubricant temperature. In some embodiments, the lubricant dilution thresholds may include a lubricant dilution temperature threshold for performing the method 300. For example, module 108 may perform method 300, as detailed below, when a value indicative of lubricant temperature (e.g., coolant temperature) is greater than 75° C. The lubricant dilution thresholds may also include thresholds for determining a cause and/or location of dilution. For example, the lubricant dilution thresholds may include one or more exhaust temperature thresholds. The one or more exhaust temperature thresholds may be used to indicate that a fuel injector of engine 12 is leaking. For example, if the fuel injector is leaking, the corresponding cylinder receiving the fuel from the injector may misfire. Consequently, non-combusted air-fuel mixture may be displaced into the exhaust system and the exhaust temperature will increase above the one or more exhaust temperature thresholds.

Debounce thresholds may include predetermined time values for which a condition must be met for the predetermined amount of time to avoid false triggers in lubricant dilution detection method 300, as detailed below. Further, to reduce noise in the data, the debounce thresholds may include one or more noise reduction thresholds. The noise reduction thresholds may include a predetermined amount of time before module 108 performs method 300 after a change in engine speed. For example, when engine system 10 shifts from high idle (e.g., 1800-1960 RPM) to low idle (e.g., 700 RPM), module 108 may wait the predetermined amount of time (e.g., sixty seconds) after the shift before performing method 300. The noise reduction thresholds may also include an engine speed deviation threshold (e.g., 10 RPM). For example, module 108 may perform method 300 when a deviation in the engine speed is less than the engine speed deviation threshold. The noise reduction thresholds may also include a threshold (e.g., 10 seconds) for reducing sensor noise. For example, module 108 may use an average of the sensed lubricant pressure from lubricant pressure signal 110 over ten seconds. It is understood that the debounce thresholds may include any value as necessary for a respective application.

Lubricant dilution indication signal 120 may include control of aspects of engine system 10. For example, lubricant dilution indication signal 120 may include controller 104 outputting a signal to display a value indicative of lubricant dilution in lubrication system 14 on output indicator 16 (e.g., on a display). Lubricant dilution indication signal 120 may also include controller 104 outputting an alert, such as a light, an audible alert, an alert on a display, or the like when there is lubricant dilution. The lubricant dilution indication signal 120 may also include mitigation or remediation recommendations. For example, module 108 may recommend service intervals, lubrication system tests, fuel system tests, and/or any other maintenance techniques for locating, mitigating, and/or remediating the cause of the lubricant dilution. For example, module 108 may determine a cause of the dilution if the exhaust temperature exceeds the exhaust temperature thresholds, as detailed below. Lubricant dilution indication signal 120 may also include controller 104 adjusting the engine system 10. For example, controller 104 may derate or shut down engine system 10 or portions thereof.

INDUSTRIAL APPLICABILITY

The disclosed aspects of the lubricant dilution detection system 100 of the present disclosure may be used in any lubrication system 14 that supplies pressurized lubricant.

Referring to FIG. 1, during the operation of engine system 10, engine 12 may drive pump 20 such that pump 20 may draw lubricant from lubricant supply 18. Pump 20 may thus provide pressurized lubricant out of pump 20 to components of engine 12 through supply line 24 such that the components of engine 12 are lubricated. For example, as engine speed increases, pump 20 speed may increase such that lubricant pressure increases. During operation of engine system 10, the pressurized lubricant may be regulated at a predetermined pressure in supply line 24 by valve 26 at certain engine speeds, as detailed above. For example, when the engine speed increases over a predetermined value, valve 26 may open proportionally such that the lubricant pressure does not exceed a predetermined pressure value (e.g., 600 kPa). In some instances, the lubricant may become diluted such that the viscosity of the lubricant decreases due to various causes, as detailed above. For example, coolant from a lubricant cooler of the lubrication system 14 and/or fuel (e.g., diesel) from one or more fuel injectors of the fuel system of the engine 12 may leak into the lubricant supply 18. The coolant and/or the fuel may have a lower viscosity than the lubricant such that the viscosity of the lubricant-coolant/fuel mixture is lower than the viscosity of the lubricant itself. When the lubricant is diluted, the components of the engine 12 may become damaged due the reduced lubrication ability of the lubricant. Further, as valve 26 regulates the lubricant pressure at relatively higher engine speeds, it may be difficult to detect lubricant dilution when valve 26 is open. For example, the lubricant pressure may build to the predetermined value to open valve 26 even if the lubricant is diluted. Therefore, lubricant dilution may not be adequately detected during relatively higher engine speeds when valve 26 is open (e.g., during the high idle condition). Further, a fixed (e.g., constant, non-varying) lubricant pressure threshold may be inadequate in determining lubricant dilution and may allow for false positives (e.g., determination of lubricant dilution when no dilution actually exists) and/or false negatives (e.g., no determination of lubricant dilution when dilution actually exists) in certain operating conditions. Thus, as detailed below with reference to FIG. 3, lubricant dilution detection system 100 may detect lubricant dilution during a low idle condition when valve 26 is closed (e.g., at engine speeds less than 800 RPM) using a varying lubricant pressure threshold.

Figure 3:
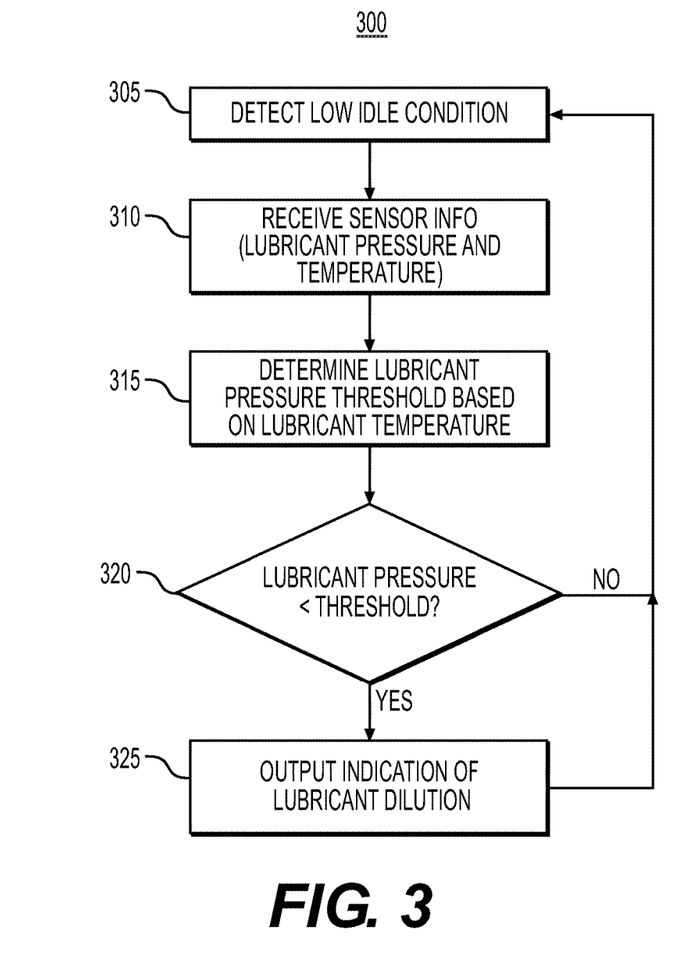
FIG. 3 provides a flowchart depicting an exemplary method for detecting dilution of a lubricant for the system of FIG. 1.

FIG. 3 illustrates a flowchart depicting an exemplary method 300 for detecting lubricant dilution for lubrication system 14. In step 305, module 108 may detect a low idle condition of engine system 10. For example, module 108 may determine the low idle condition when the engine speed is substantially equal to 700 RPM. As detailed above, module 108 may utilize other operating condition parameters and respective low idle condition thresholds. In accordance with a determination that a respective operating condition is substantially equal to the respective low idle condition threshold, module 108 may determine a low idle condition of engine system 10. It is understood that module 108 may detect a low idle condition of engine system 10 by any other method known in the art.

In step 310, when module 108 has detected a low idle condition, module 108 may receive sensor information. For example, module 108 may receive the lubricant pressure signal 110, the lubricant temperature signal 112, and the engine speed signal 114 during the low idle condition and determine, or otherwise derive, sensed values of the lubricant pressure, the lubricant temperature, and the engine speed, respectively. Module 108 may also determine a rate of lubricant pressure change over time based on the lubricant pressure signal 110 and a rate of lubricant temperature change over time based on the lubricant temperature signal 112.

In step 315, module 108 may determine the lubricant pressure threshold based on the lubricant temperature. For example, module 108 may receive the values indicative of lubricant temperature (e.g., lubricant temperature and/or coolant temperature), and use the map or lookup table, as detailed above, to determine the lubricant pressure threshold based on the received value indicative of lubricant temperature.

In step 320, when the lubricant pressure threshold has been determined, module 108 may determine whether the sensed value of lubricant pressure is less than the threshold (e.g., the lubricant pressure threshold). For example, when there is no dilution, or negligible dilution, the sensed value of lubricant pressure will be above the respective lubricant dilution threshold during the low idle condition. Thus, when the sensed value of lubricant pressure is greater than or equal to the threshold (Step 320: NO), module 108 may repeat the method 300 and continue to detect low idle conditions (step 305).

When the lubricant is diluted, the lubricant pressure may decrease below the respective lubricant dilution threshold during the low idle condition. Thus, in step 325, in accordance with a determination that the sensed value of lubricant pressure is less than the threshold (Step 320: YES), module 108 may output an indication of lubricant dilution. For example, module 108 may display the indication of the lubricant dilution on output indicator 16 (e.g., on a display and/or as a notification, such as a light, an audible alert, an alert on a display, etc.). Module 108 may then repeat the method 300 and continue to detect low idle conditions (step 305). In some embodiments, module 108 may derate the engine system 10, send a signal to shut down engine system 10, and/or may output an indication of a cause of the dilution, as detailed further below.

Figure 4:
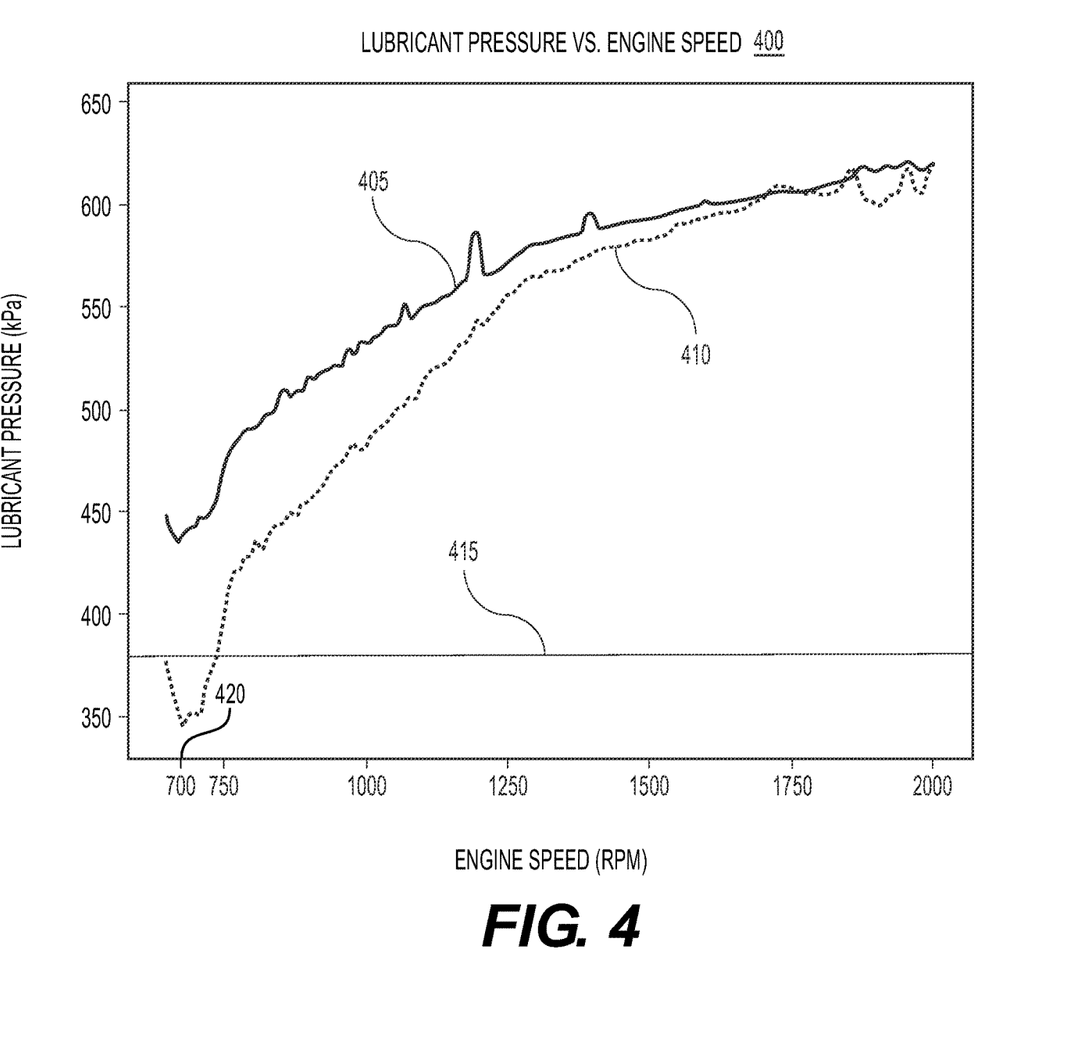
FIG. 4 is a plot of lubricant pressure versus engine speed, according to aspects of the disclosure.

Module 108 may store values or instances of the lubricant pressure during a plurality of low idle conditions. For example, module 108 may detect several different low idle conditions and store values of the lubricant pressure. Referring to FIG. 4, module 108 may generate a plot 400 of the lubricant pressure for the different low idle conditions over time. Plot 400 may include a graphical representation of various data points 405, 410 of the lubricant pressure for various engine speeds. First data points 405 indicate the relationship of lubricant pressure and engine speed when there is no, or negligible, lubricant dilution. Second data points 410 indicate a relationship of lubricant pressure and engine speed when there is lubricant dilution. In the exemplary embodiment of FIG. 4, the lubricant dilution threshold 415 of the exemplary embodiment in FIG. 4 is 375 kPa (e.g., as determined by the lubricant temperature). Further, the low idle condition 420 in this example is 700 RPM. As shown in FIG. 4, the lubricant pressure is regulated at 600 kPa for greater engine speeds (e.g., during high idle). For example, at the greater engine speeds, the valve 26 is opened such that the lubricant pressure is regulated. A drop in lubricant pressure between the first data points 405 and second data points 410 is more noticeable when the valve 26 is closed (e.g., during the low idle condition—700 RPM). Thus, plot 400 illustrates that the lubricant pressure (e.g., data points 410) will decrease below the threshold 415 during the low idle condition, and therefore module 108 may determine that there is lubricant dilution. It is understood that plot 400 may include a plot of lubricant pressure versus any other operating condition.

To further reduce or eliminate false positives and/or false negatives of lubrication dilution detection, as detailed above, module 108 may also include debounce thresholds. For example, module 108 may determine lubricant dilution when the lubricant pressure is less than the lubricant pressure threshold for a predetermined amount of time (e.g., 3 seconds). Similarly, module 108 may also include an amount of data points 410 that required to be less than the lubricant pressure threshold as a function of the total amount of data points 410. For example, if 3 out of 15 data points fall below the lubricant pressure threshold, module 108 may determine lubricant dilution.

Module 108 may also determine a cause of the lubricant dilution. For example, as detailed above, module 108 may receive the exhaust temperature pressure signal 116 and determine, or otherwise derive, sensed values of the exhaust temperature. Module 108 may then determine a cause of the lubricant dilution based on the sensed values of exhaust temperature. For example, module 108 may determine if the sensed values of exhaust temperature are greater than an exhaust temperature threshold. If the sensed values of exhaust temperature are greater than the exhaust temperature threshold, module 108 may determine that one or more fuel injectors are leaking fuel into the lubricant system 14, and thus causing the lubricant dilution. In some embodiments in which the engine system 10 includes a first exhaust and a second exhaust (e.g., different exhaust manifolds having different exhaust temperature sensors), module 108 may receive sensed values of exhaust temperatures of both the first exhaust and the second exhaust. Thus, module 108 may determine at least one of the first exhaust and/or the second exhaust includes an exhaust temperature greater than the exhaust temperature threshold. Therefore, module 108 may determine a location of the leaking fuel injector based on which exhaust includes the increased exhaust temperature. For example, if the first exhaust is greater than the exhaust temperature threshold, module 108 may determine the leaking fuel injector is located on a side of engine 12 that the first exhaust is located.

Lubricant dilution detection system 100 may provide an indication of lubricant dilution in lubrication system 14. For example, lubricant dilution detection system 100 may detect lubricant dilution due to, for example, fuel leaks in a fuel system of engine 12, coolant leaks from a lubricant cooler, age of the lubricant, and/or any other causes of dilution. Further, by detecting lubricant dilution during low idle conditions, lubricant dilution detection system 100 may ensure that valve 26 is closed such that system 100 may more adequately detect lubricant dilution. Lubricant dilution detection system 100 may also reduce or eliminate false positives and/or false negatives by using a variable lubricant pressure threshold based on lubricant temperature. Accordingly, lubricant dilution detection system 100 may more accurately or adequately detect lubricant dilution (e.g., and cause and/or location of the lubricant dilution) in lubrication system 14 and proactively alert a user (e.g., operator, technician, etc.) so that the user may repair and/or replace the respective component to mitigate the lubrication dilution.

It will be apparent to those skilled in the art that various modifications and variations can be made to the disclosed system without departing from the scope of the disclosure. Other embodiments of the system will be apparent to those skilled in the art from consideration of the specification and practice of the system disclosed herein. It is intended that the specification and examples be considered as exemplary only, with a true scope of the disclosure being indicated by the following claims and their equivalents.

What is claimed is:

1. A method for detecting lubricant dilution for a lubrication system, comprising:
   detecting a low idle condition in which a pressure regulator valve of the lubrication system is closed;
   receiving sensed values indicative of lubricant pressure and lubricant temperature during the low idle condition;
   determining a lubricant pressure threshold based on the sensed value indicative of lubricant temperature;
   determining lubricant dilution based on the sensed value indicative of lubricant pressure and the determined lubricant pressure threshold during the low idle condition; and
   in accordance with a determination that there is lubricant dilution, outputting an indication of the lubricant dilution.

2. The method of claim 1, wherein detecting the low idle condition includes detecting an engine speed is substantially equal to a low idle engine speed threshold.

3. The method of claim 2, wherein detecting the low idle condition includes:
   receiving sensed values indicative of engine speed; and
   detecting the low idle condition when the sensed values indicative of engine speed change from a high idle condition to the low idle condition after a predetermined amount of time.

4. The method of claim 1, wherein the lubricant pressure threshold is determined based on a map representative of empirical data of lubricant pressure threshold values with respect to a value indicative of lubricant temperature.

5. The method of claim 1, further including:
   determining lubricant dilution based on a plurality of low idle conditions.

6. The method of claim 1, wherein determining lubricant dilution includes:
   determining whether the sensed value indicative of lubricant pressure is less than the determined lubricant pressure threshold; and
   in accordance with a determination that the sensed value indicative of lubricant pressure is less than the lubricant pressure threshold, determining lubricant dilution.

7. The method of claim 6, wherein the lubricant pressure threshold is a variable threshold including different threshold values for different values of lubricant temperature.

8. The method of claim 6, further including:
   receiving sensed values indicative of lubricant pressure over time during the low idle condition; and
   determining lubricant dilution when the sensed values indicative of lubricant pressure are less than the determined lubricant pressure threshold for a predetermined amount of time.

9. The method of claim 1, further including:
receiving sensed values indicative of exhaust temperature during the low idle condition; and
determining a cause of the lubricant dilution based on the sensed values indicative of exhaust temperature.

10. The system of claim 1, wherein the pressure regulator valve is open to regulate lubricant pressure during the high idle condition.

11. A lubricant dilution detection system, comprising:
a lubrication system comprising a pressure regulator valve that is closed in a low idle condition of an engine;
a lubricant pressure sensor for sensing values indicative of lubricant pressure in the lubrication system;
a lubricant temperature sensor for sensing values indicative of lubricant temperature in the lubrication system; and
a controller configured to:
detect the low idle condition;
receive the sensed values indicative of lubricant pressure and lubricant temperature during the low idle condition;
determine a lubricant pressure threshold based on the sensed value indicative of lubricant temperature;
determine lubricant dilution based on the sensed value indicative of lubricant pressure and the determined lubricant pressure threshold during the low idle condition; and
in accordance with a determination that there is lubricant dilution, output an indication of the lubricant dilution.

12. The system of claim 11, wherein detecting the low idle condition includes the controller configured to:
detect an engine speed is substantially equal to a low idle engine speed threshold.

13. The system of claim 12, wherein detecting the low idle condition includes the controller configured to:
receive sensed values indicative of engine speed; and
detect the low idle condition when the sensed values indicative of engine speed change from a high idle condition to the low idle condition after a predetermined amount of time.

14. The system of claim 11, wherein the lubricant pressure threshold is determined based on a map representative of empirical data of lubricant pressure threshold values with respect to a value indicative of lubricant temperature.

15. The system of claim 11, wherein the controller is further configured to:
determine lubricant dilution based on a plurality of low idle conditions.

16. The system of claim 11, wherein determining lubricant dilution includes the controller configured to:
determine whether the sensed value indicative of lubricant pressure is less than the determined lubricant pressure threshold; and
in accordance with a determination that the sensed value indicative of lubricant pressure is less than the lubricant pressure threshold, determine lubricant dilution.

17. The system of claim 16, wherein the lubricant pressure threshold is a variable threshold including different threshold values for different values indicative of lubricant temperature.

18. The system of claim 16, wherein the controller is further configured to:
receive sensed values indicative of lubricant pressure over time during the low idle condition; and
determine lubricant dilution when the sensed values indicative of lubricant pressure are less than the determined lubricant pressure threshold for a predetermined amount of time.

19. The system of claim 11, wherein the controller is further configured to:
receive sensed values indicative of exhaust temperature during the low idle condition; and
determine a cause of the lubricant dilution based on the sensed values indicative of exhaust temperature.

20. A method for detecting lubricant dilution for a lubrication system, comprising:
detecting a low idle condition of an engine when an engine speed is substantially equal to a low idle engine speed threshold;
receiving sensed values indicative of lubricant pressure over time during the low idle condition;
receiving a sensed value indicative of lubricant temperature during the low idle condition;
determining a lubricant pressure threshold based on the sensed value indicative of lubricant temperature, wherein the lubricant pressure threshold is a variable threshold including different threshold values for different values indicative of lubricant temperature;
determining whether the sensed values indicative of lubricant pressure are less than the determined lubricant pressure threshold during the low idle condition for a predetermined amount of time;
in accordance with a determination that the sensed values indicative of lubricant pressure are less than the determined lubricant pressure threshold for the predetermined amount of time, determining lubricant dilution; and
in accordance with a determination that there is lubricant dilution, outputting an indication of the lubricant dilution.

* * * * *